(12) United States Patent
Hillman et al.

(10) Patent No.: US 6,323,328 B1
(45) Date of Patent: Nov. 27, 2001

(54) HUMAN CITRATE SYNTHASE HOMOLOG

(75) Inventors: Jennifer L. Hillman, Mountain View; Preeti Lal, Santa Clara; Neil C. Corley, Mountain View; Purvi Shah, Sunnyvale, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 08/970,134

(22) Filed: Nov. 13, 1997

(51) Int. Cl.$^7$ .......................... C12N 15/11; C12N 15/63; C12N 1/21; C12N 15/00

(52) U.S. Cl. .................. 536/23.1; 435/320.1; 435/252.3; 435/69.1

(58) Field of Search ........................ 536/23.1; 435/320.1, 435/252.3, 69.1

(56) References Cited

PUBLICATIONS

Wiegand, G. and Remington, S. J. "CITRATE SYNTHASE: Structure, Control, and Mechanism" *Ann.Rev.Biophys.Chem.* (1986) 15:97–117.

Karpusas, M. et al., "Proposed Mechanism for the Condensation Reaction of Citrate Synthase: 1.9–Å Structure of the Ternary Complex with Oxaloacetate and Carboxymethyl Coenzyme A" *Biochemistry* (1990) 29:2213–2219.

Oudard, S. et al., "Gliomas are Driven by Glycolysis: Putative Roles of Hexokinase, Oxidative Phosphorylation and Mitochondrial Ultrastructure" *Anticancer Research* (1997) 17:1903–1912.

Simoneau, J.–A. and Kelley, D.E., "Altered glycolytic and oxidative capacities of skeleal muscle contribute to insulin resistance in NIDDM" *J.Appl.Physiol.* (1997) 83:166–171.

Pastoris, O. et al., "Altered Muscle Energy Metabolism in Post–absorptive Patients with Chronic Renal Failure" *Scan.J.Urol.Nephrol.* (1997) 31:281–287.

Conjard, A. et al., "Effects of Chronic Renal Failure on Enzymes of Energy Metabolism in Individual Human Muscle Fibers" *J.Am.Soc.Nephrol.* (1995) 6:68–74.

Sangiorgi, S. et al., "Abnormal platelet mitochondrial function in patients affected by migraine with and without aura" *Cephalalgia* (1994) 14:21–23.

Rooyackers, O.E. et al., "Effect of age on *in vivo* rates of mitochondrial protein synthesis in human skeletal muscle" *Proc.Natl.Acad.Sci.USA* (1996) 93:15364–15369.

Coyle, E.F. et al., "Time course of loss of adaptions after stopping prolonged intense endurance training" *J.Appl.Physiol.* (1984) 57:1857–1864.

Evans, C.T. et al., GI 164418, GenBank, Sequence Database (Accession M21197), National Center for Biotechnology Information, National Library of Medicine, Bethesda, Maryland, 20894.

Evans, C.T. et al., "Isolation, Nucleotide Sequence, and Expression of a cDNA Encoding Pig Citrate Synthase" *Biochemistry* (1988) 27:4680–4686.

Srere, P.A., "Citrate Synthetase" *Methods in Enzymology* (1969) 13:3–11.

*Primary Examiner*—Paula K. Hutzell
*Assistant Examiner*—Susan Ungar
(74) *Attorney, Agent, or Firm*—Incyte Genomics, Inc.

(57) ABSTRACT

The invention provides a human citrate synthase homolog (HUCS) and polynucleotides which identify and encode HUCS. The invention also provides expression vectors, host cells, agonists, antibodies and antagonists. The invention also provides methods for treating disorders associated with expression of HUCS.

8 Claims, 8 Drawing Sheets

```
                                                                      54
5' NCG CCG GTT CGT CTA CTC TTT CCT TCA GCC GCC TCC TTT CAA CCT TGT CAA CCC

108
GTC GGC GCG GCC TCT GGT GCA GCG GCG GCT CCT GTT CCT GCC GCA GCT CTC

162
TCC CTT TCT TAC CTC CCC ACC AGA TCC CGG AGA TCG CCC GCC ATG GCT TTA CTT
                                                                  M   A   L   L

216
ACT GCG GCC GCC CGG CTC TTG GGA CTC AAG AAT AAT GCA TCT TGT CTT GTT CTT GCA
 T   A   A   A   R   L   L   G   T   K   N   A   S   C   L   V   L   A

270
GCC CGG CAT GCC AGT GCT TCC TCC ACG AAT TTG AAA GAC ATA TTG GCT GAC CTG
 A   R   H   A   S   S   T   N   L   K   D   I   L   A   D   L

324
ATA CCT AAG GAG CAG GCC AGA ATT AAG ACT TTC AGG CAG CAA CAT GGC AAG ACG
 I   P   K   E   Q   A   R   I   K   T   F   R   Q   Q   H   G   K   T

378
GTG GTG GGC CAA ATC ACT GTG GAC ATG ATG TAT GGT GGC ATG AGA GGC ATG AAG
 V   V   G   Q   I   T   V   D   M   M   Y   G   G   M   R   G   M   K
```

FIGURE 1A

```
                387       396       405       414       423       432
GGA TTG GTC TAT GAA ACA TCA GTT CTT GAT CCT GAT GAG GGC ATC CGT TTC CGA
 G   L   V   Y   E   T   S   V   L   D   P   D   E   G   I   R   F   R 441       450       459       468       477       486
GGC TTT AGT ATC CCT GAA TGC CAG AAA CTG CTA CCC AAG GCT AAG GGT GGG GAA
 G   F   S   I   P   E   C   Q   K   L   L   P   K   A   K   G   G   E 495       504       513       522       531       540
GAA CCC CTG CCT GAG GGC TTA TTT TGG CTG CTG GTA ACT GGA CAT ATC CCA ACA
 E   P   L   P   E   G   L   F   W   L   L   V   T   G   H   I   P   T 549       558       567       576       585       594
GAG GAA CAG GTA TCT GAG CTC TCA AAA GAG TGG GCA AAG AGG GCA GCT CTG CCT
 E   E   Q   V   S   E   L   S   K   E   W   A   K   R   A   A   L   P 603       612       621       630       639       648
TCC CAT GTG GTC ACC ATG CTG GAC AAC TTT CCC ACC AAT CTA CAC CCC ATG TCT
 S   H   V   V   T   M   L   D   N   F   P   T   N   L   H   P   M   S 657       666       675       684       693       702
CAG CTC AGT GCA GCT GTT ACA GCC CTC AAC AGT GAA AGT AAC TTT GCC CGA GCA
 Q   L   S   A   A   V   T   A   L   N   S   E   S   N   F   A   R   A 711       720       729       738       747       756
TAT GCA CAG GGT ATC AGC CGA ACC AAG TAC TGG GAG TTG ATT TAT GAA GAC TCT
 Y   A   Q   G   I   S   R   T   K   Y   W   E   L   I   Y   E   D   S
```

FIGURE 1B

```
      765         774         783         792         801         810
ATG GAT CTA ATC GCA AAG CTA CCT TGT GTT GCA AAG ATC TAC CGA AAT CTC
 M   D   L   I   A   K   L   P   C   V   A   K   I   Y   R   N   L 819         828         837         846         855         864
TAC AGA GAA GGC AGC ATG GGT ATT GCC ATT GAC TCT AAC CTG GAC TGG TCT CAC
 Y   R   E   G   S   M   G   I   A   I   D   S   N   L   D   W   S   H 873         882         891         900         909         918
AAT TTC ACC AAC ATG TTA GGC TAT ACT GAT CAT CAG TTC ACT GAG CTC ACG CGC
 N   F   T   N   M   L   G   Y   T   D   H   Q   F   T   E   L   T   R 927         936         945         954         963         972
CTG TAC CTC ACC ATC CAC AGT GAC CAT GAG GGT GGC AAT GTA AGT GCC CAT ACC
 L   Y   L   T   I   H   S   D   H   E   G   G   N   V   S   A   H   T 981         990         999        1008        1017        1026
AGC CAT TTG GTG GGC AGT GCC CTT TCC GAC CCT TAC CTG TCC TTT GCA GCA GCC
 S   H   L   V   G   S   A   L   S   D   P   Y   L   S   F   A   A   A 1035        1044        1053        1062        1071        1080
ATG AAC GGG CTG GCA GGG CCT CTC CAT GGA CTG GCA AAT CAG GAA GTG CTT GTC
 M   N   G   L   A   G   P   L   H   G   L   A   N   Q   E   V   L   V 1089        1098        1107        1116        1125        1134
TGG CTA ACA CAG CTG CAG AAG GAA GTT GGC AAA GAT GTG TCA GAT GAG AAG TTA
 W   L   T   Q   L   Q   K   E   V   G   K   D   V   S   D   E   K   L
```

FIGURE 1C

```
                   1143           1152           1161           1170           1179           1188
                   CGA GAC TAC ATC TGG AAC ACA CTC AAC TCA GGA CGG GTT GTT CCA GGC TAT GGC
                    R   D   Y   I   W   N   T   L   N   S   G   R   V   V   P   G   Y   G
                   1197           1206           1215           1224           1233           1242
                   CAT GCA GTA CTA AGG AAG ACT GAT CCG CGA TAT ACC TGT CAG CGA GAG TTT GCT
                    H   A   V   L   R   K   T   D   P   R   Y   T   C   Q   R   E   F   A
                   1251           1260           1269           1278           1287           1296
                   CTG AAA CAC CTG CCT AAT GAC CCC ATG TTT AAG TTG GTT GCT CAG CTG TAC AAG
                    L   K   H   L   P   N   D   P   M   F   K   L   V   A   Q   L   Y   K
                   1305           1314           1323           1332           1341           1350
                   ATT GTG CCC AAT GTC CTC TTA GAG CAG GGT AAA GCC AAG AAT CCT TGG CCC AAT
                    I   V   P   N   V   L   L   E   Q   G   K   A   K   N   P   W   P   N
                   1359           1368           1377           1386           1395           1404
                   GTA GAT GCT CAC AGT GGG GTG CTG CTC CAG TAT TAT GGC ATG ACG GAG ATG AAT
                    V   D   A   H   S   G   V   L   L   Q   Y   Y   G   M   T   E   M   N
                   1413           1422           1431           1440           1449           1458
                   TAC TAC ACG GTC CTG TTT GGG TCA CGA GCA TTG GGT GTA GCA CTG GCA CAG CTC
                    Y   Y   T   V   L   F   G   S   R   A   L   G   V   A   L   A   Q   L
                   1467           1476           1485           1494           1503           1512
                   ATC TGG AGC CGA GCC TTA GGC TTC CCT CTA GAA AGG CCC AAG ATG AGC ACA
                    I   W   S   R   A   L   G   F   P   L   E   R   P   K   M   S   T
```

FIGURE 1D

```
      1521            1530            1539            1548            1557       1566
GAG GGT ATG AAG TTT GTG GAC TCT AAG TCA GGG TAA AAC TGG AGA CTG GGT
 E   G   M   K   F   V   D   S   K   S   G   *

1575            1584            1593            1602            1611       1620
GAA AGT GAC TAC CAG AAA GTG AGG AAG CCT AAA TAA AAA GTA TAC TTT TGT TTC 1629            1638            1647            1656            1665       1674
AGG GGG CCT TTA AAG ACT TAA GAT TAA ATT ATA TCT GAG GCA CTG ATA ATA TGT 1683            1692            1701            1710            1719       1728
TTG AGG TTA AAA TAT AAA TTA AGA CTT TAA AAG ATG AAA AAT GGT CCC TTC TTC 1737            1746            1755            1764            1773       1782
CCT AAT CAG CTC CCT TCC CCT GCC TGG TAT GAG TTG CCC ATC ATA CGC ATG GTC 1791            1800            1809            1818            1827       1836
CTG GAG GAT GAC CAG GAC TAA TGC ATG TGG TAT GAG TAG GTT TGG CCC CCT CAC 1845            1854            1863            1872            1881       1890
TAT CTC TAG AGT GAG AAT CTG GCT CCT GTT TCC ATG GGT CAA AGC CGG TTG CAG
```

FIGURE 1E

```
        1899           1908           1917      1926      1935      1944
AGA ATC TGT AGT CAC TTT GGA GCT TTA GCT TCT CTG CCA AGC CCT CAA TAA GCC 1953           1962           1971      1980      1989      1998
AGC AAA CCA GGA CTC TGC CCC TTC TGT TTC CAT AGG AAT CAT GTT GGA TAG TCA 2007           2016           2025      2034      2043      2052
GCT GTA CCA AGC CCC TTG GCC CTC TCC CAT GCA CAC AAA CAC CTC CTA GCA AGA 2061           2070           2079      2088      2097      2106
CCT GTT GGT TAG CTG GAC ATG CTT TGG CAA TTT TTT TAT ACT ACC AAG TGA CCA 2115           2124
TAT TGG CAT GGC ATT TTT TGG TGA TG 3'
```

FIGURE 1F

| | | |
|---|---|---|
| 1 | M A L L T A A A R L L G T K N A S C L V | 2171653 |
| 1 | M A L L T A A A R L F G A K N A S C L V | GI 164419 |
| 21 | L A A R H A S A S S T N L K D I L A D L | 2171653 |
| 21 | L A A R H A S A S S T N L K D I L A D L | GI 164419 |
| 41 | I P K E Q A R I K T F R Q Q H G K T V V | 2171653 |
| 41 | I P K E Q A R I K T F R Q Q H G N T V V | GI 164419 |
| 61 | G Q I T V D M M Y G G M R G M K G L V Y | 2171653 |
| 61 | G Q I T V D M M Y G G M R G M K G L V Y | GI 164419 |
| 81 | E T S V L D P D E G I R F R G F S I P E | 2171653 |
| 81 | E T S V L D P D E G I R F R G Y S I P E | GI 164419 |
| 101 | C Q K L L P K A K G G E E P L P E G L F | 2171653 |
| 101 | C Q K M L P K A K G G E E P L P E G L F | GI 164419 |
| 121 | W L L V T G H I P T E E Q V S W L S K E | 2171653 |
| 121 | W L L V T G Q I P T E E Q V S W L S K E | GI 164419 |
| 141 | W A K R A A L P S H V V T M L D N F P T | 2171653 |
| 141 | W A K R A A L P S H V V T M L D N F P T | GI 164419 |
| 161 | N L H P M S Q L S A A V T A L N S E S N | 2171653 |
| 161 | N L H P M S Q L S A A I T A L N S E S N | GI 164419 |
| 181 | F A R A Y A Q G I S R T K Y W E L I Y E | 2171653 |
| 181 | F A R A Y A E G I H R T K Y W E L I Y E | GI 164419 |
| 201 | D S M D L I A K L P C V A A K I Y R N L | 2171653 |
| 201 | D C M D L I A K L P C V A A K I Y R N L | GI 164419 |
| 221 | Y R E G S G I G A I D S N L D W S H N F | 2171653 |
| 221 | Y R E G S S I G A I D S K L D W S H N F | GI 164419 |

HUMAN CITRATE SYNTHASE HOMOLOG

FIELD OF THE INVENTION

This invention relates to nucleic acid and amino acid sequences of a human citrate synthase homolog and to the use of these sequences in the diagnosis, prevention, and treatment of cancer, inflammatory disorders, and disorders of the sympathetic nervous system.

BACKGROUND OF THE INVENTION

Cells obtain energy in the form of ATP through the enzymatic degradation of glucose. This process begins with the glycolytic pathway in the cytosol when glucose is converted to pyruvate. Subsequently pyruvate is transported to mitochondria and converted to acetyl-CoA. Acetyl-CoA, whether obtained through the breakdown of glucose, fatty acids or amino acids, enters the citric acid cycle and, through the action of seven different enzymes, is converted to carbon dioxide and water. The citric acid cycle produces ATP, NADH and $FADH_2$, and intermediates needed in lipogenesis, gluconeogenesis, and in the biosynthesis of amino acids.

Citrate synthase, the first enzyme in the citric acid cycle, catalyzes the condensation of acetyl-CoA with oxaloacetate to form citrate and Coenzyme A (CoASH). This reaction, the rate-limiting step of the citric acid cycle in many cells, is regulated by concentrations of acetyl-CoA, oxaloacetate, citrate, succinyl-CoA, and NADH. Pig citrate synthase has been purified and its amino acid sequence, three-dimensional structure, and mechanism determined (cf. Wiegand, G. and Remington, S. J. (1986) Ann. Rev. Biophys. Biophys. Chem. 15: 97–117). Citrate synthase is encoded by the nuclear DNA, translated in the cytosol, and transported into mitochondria via a leader sequence. The leader is cleaved to release the mature citrate synthase which localizes to the mitochondrial inner membrane. A sequence of thirteen amino acids surrounding the active site histidine is conserved among eukaryotic and prokaryotic citrate synthases (Karpusas, M. et al. (1990) Biochemistry 29:2213–2219). The active enzyme is a dimer of identical subunits found in nearly all living cells.

Citrate synthase activity can be measured in human tissue, and lowered citrate synthase activity is associated with cancer. Human glioblastoma multiforme (glioma), the most frequent malignant primary brain tumor, has increased glycolytic metabolism (Oudard, S. et al. (1997) Anticancer Research 17:1903–1912). When human glioma cells are transplanted into rat brain, citrate synthase activity is lower in the tumors than in normal rat brain. When the tumor cells are examined by electron microscopy, mitochondria are fewer in number than in normal rat brain and have altered morphology. The research suggests that the lowered number of mitochondria in glioma cells explains the reduced citrate synthase and increased glycolytic activities of these cells.

Lowered citrate synthase activity is associated with non-insulin-dependent diabetes mellitus (NIDDM). Patients with NIDDM, many of whom are obese, have lower citrate synthase activity in muscle biopsies than those of either lean or obese control subjects (Simoneau, J.-A. and Kelley, D. E. (1997) J. Appl. Physiol. 83: 166–171). Citrate synthase activity is also altered in patients with chronic renal failure. Chronic renal failure (CRF) is caused by a number of diseases, including chronic pyelonephritis, nephroangiosclerosis, chronic glomerulonephritis, polycystic kidney disease, and Alport's syndrome (Pastoris, O. et al. (1997) Scand. J. Urol. Nephrol. 31: 281–287). CRF patients often exhibit muscle weakness and fatigue, and citrate synthase activity in CRF patient muscle biopsies has been reported as lower than control (Conjard, A. et al. (1995) J. Am. Soc. Nephrol. 6: 68–74).

Lowered citrate synthase activity is associated with migraine headache. Patients who suffer from migraine, with and without aura, have lower citrate synthase activity in their platelet mitochondria than do controls (Sangiorgi, S. et al. (1994) Cephalalgia 14: 21–23). The authors suggest that this reduction in citrate synthase activity in migraine patients indicates a general impairment in energy metabolism and mitochondrial function.

Humans exhibit declining muscle mass and performance as they age. These traits are associated with a decrease in the activities of mitochondrial enzymes, including citrate synthase (Rooyackers, O. E. et al. (1996) Proc. Natl. Acad. Sci. USA 93:15364–15369). Citrate synthase activity was decreased in muscle homogenates and isolated mitochondria and suggests a decline in both muscle oxidative capacity and mitochondrial function. A reduction in physical activity also lowers citrate synthase activity. When endurance exercise-trained subjects stopped their physical training, their citrate synthase activity dropped (Coyle, E. F. et al. (1984) J. Appl. Physiol. 57: 1857–1864).

The discovery of a new human citrate synthase homolog and the polynucleotides encoding it satisfies a need in the art by providing new compositions which are useful in the diagnosis, prevention, and treatment of cancer, inflammatory disorders, and disorders of the sympathetic nervous system.

SUMMARY OF THE INVENTION

The invention features a substantially purified polypeptide, human citrate synthase homolog (HUCS), comprising the amino acid sequence of SEQ ID NO:1 or a fragment of SEQ ID NO:1.

The invention further provides a substantially purified variant of HUCS having at least 90% amino acid identity to the amino acid sequence of SEQ ID NO:1 or a fragment of SEQ ID NO:1. The invention also provides an isolated and purified polynucleotide sequence encoding the polypeptide comprising the amino acid sequence of SEQ ID NO:1 or a fragment of SEQ ID NO:1. The invention also includes an isolated and purified polynucleotide variant having at least 90% polynucleotide identity to the polynucleotide sequence encoding the polypeptide comprising the amino acid sequence of SEQ ID NO:1 or a fragment of SEQ ID NO:1.

Additionally, the invention provides a composition comprising a polynucleotide sequence encoding the polypeptide comprising the amino acid sequence of SEQ ID NO:1 or a fragment of SEQ ID NO:1. The invention further provides an isolated and purified polynucleotide sequence which hybridizes under stringent conditions to the polynucleotide sequence encoding the polypeptide comprising the amino acid sequence of SEQ ID NO:1 or a fragment of SEQ ID NO:1, as well as an isolated and purified polynucleotide sequence which is complementary to the polynucleotide sequence encoding the polypeptide comprising the amino acid sequence of SEQ ID NO:1 or a fragment of SEQ ID NO:1.

The invention also provides an isolated and purified polynucleotide sequence comprising SEQ ID NO:2 or a fragment of SEQ ID NO:2, and an isolated and purified polynucleotide variant having at least 90% polynucleotide identity to such a polynucleotide sequence. The invention also provides an isolated and purified polynucleotide sequence which is complementary to the polynucleotide sequence comprising SEQ ID NO:2 or a fragment of SEQ ID NO:2.

The invention further provides an expression vector containing at least a fragment of any of the claimed polynucleotide sequences. In another aspect, the expression vector containing the polynucleotide sequence is contained within a host cell.

The invention also provides a method for producing a polypeptide comprising the amino acid sequence of SEQ ID NO:1 or a fragment of SEQ ID NO:1, the method comprising the steps of: (a) culturing the host cell containing an expression vector containing at least a fragment of a polynucleotide sequence encoding HUCS under conditions suitable for the expression of the polypeptide; and (b) recovering the polypeptide from the host cell culture.

The invention also provides a pharmaceutical composition comprising a substantially purified HUCS having the amino acid sequence of SEQ ID NO:1 or a fragment of SEQ ID NO:1 in conjunction with a suitable pharmaceutical carrier.

The invention further includes a purified antibody which binds to a polypeptide comprising the amino acid sequence of SEQ ID NO:1 or a fragment of SEQ ID NO:1, as well as a purified agonist and a purified antagonist of the polypeptide.

The invention also provides a method for treating or preventing a cancer, the method comprising administering to a subject in need of such treatment an effective amount of a pharmaceutical composition comprising substantially purified HUCS.

The invention also provides a method for treating or preventing an inflammatory disorder, the method comprising administering to a subject in need of such treatment an effective amount of a pharmaceutical composition comprising substantially purified HUCS.

The invention also provides a method for treating or preventing a disorder of the sympathetic nervous system, the method comprising administering to a subject in need of such treatment an effective amount of a pharmaceutical composition comprising substantially purified HUCS.

The invention also provides a method for detecting a polynucleotide encoding HUCS in a biological sample containing nucleic acids, the method comprising the steps of: (a) hybridizing the complement of the polynucleotide sequence which encodes the polypeptide comprising SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding HUCS in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, 1E, and 1F show the amino acid sequence (SEQ ID NO:1) and nucleic acid sequence (SEQ ID NO:2) of HUCS. The alignment was produced using MacDNASIS PRO™ software (Hitachi Software Engineering Co. Ltd. San Bruno, Calif.).

FIGS. 2A and 2B show the amino acid sequence alignment between HUCS (2171653; SEQ ID NO:1) and pig citrate synthase precursor (GI 164419; SEQ ID NO:3), produced using the multisequence alignment program of DNASTAR™ software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

HUCS, as used herein, refers to the amino acid sequences of substantially purified HUCS obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to HUCS, increases or prolongs the duration of the effect of HUCS. Agonists may include proteins, nucleic acids, carbohydrates, or any other molecules which bind to and modulate the effect of HUCS.

An "allele" or "allelic sequence", as used herein, is an alternative form of the gene encoding HUCS. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HUCS as used herein include those with deletions, insertions, or substitutions of different nucleotides resulting in a polynucleotide that encodes the same or a functionally equivalent HUCS. Included within this definition are polymorphisms which may or may not be readily detectable using a particular oligonucleotide probe of the polynucleotide encoding HUCS, and improper or unexpected hybridization to alleles, with a locus other than the normal chromosomal locus for the polynucleotide sequence encoding HUCS. The encoded protein may also be "altered" and contain deletions, insertions, or substitutions of amino acid residues which produce a silent change and result in a functionally equivalent HUCS. Deliberate amino acid substitutions may be made on the basis of similarity in polarity, charge, solubility, hydrophobicity, hydrophilicity, and/or the amphipathic nature of the residues as long as the biological or immunological activity of HUCS is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of HUCS are preferably about 5 to about 15 amino acids in length and retain the biological activity or the immunological activity of HUCS. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to HUCS, decreases the amount or the duration of the effect of the biological or immunological activity of HUCS. Antagonists may include proteins, nucleic acids, carbohydrates, antibodies or any other molecules which decrease the effect of HUCS.

As used herein, the term "antibody" refers to intact molecules as well as fragments thereof, such as Fa, F(ab')$_2$, and Fv, which are capable of binding the epitopic determinant. Antibodies that bind HUCS polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic HUCS, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding HUCS (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR™ (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW™ Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 by northern analysis is indicative of the presence of mRNA encoding HUCS in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to HUCS or the encoded HUCS. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of HUCS. For example, modulation may cause an increase or a decrease in protein activity, binding characteristics, or any other biological, functional or immunological properties of HUCS.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers","primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length HUCS and fragments thereof.

The term "sample", as used herein, is used in its broadest sense. A biological sample suspected of containing nucleic acid encoding HUCS, or fragments thereof, or HUCS itself may comprise a bodily fluid, extract from a cell, chromosome, organelle, or membrane isolated from a cell, a cell, genomic DNA, RNA, or cDNA (in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

As used herein, the term "stringent conditions" refers to conditions which permit hybridization between polynucleotide sequences and the claimed polynucleotide sequences. Suitably stringent conditions can be defined by, for example, the concentrations of salt and/or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C.

to 42° C. Hybridization could occur under reduced stringency conditions in about 35% to 25% formamide at about 30° C. to 35° C. In particular, hybridization could occur under high stringency conditions at 42° C. in 50% formamide, 5X SSPE, 0.3% SDS, and 200 µg/ml sheared and denatured salmon sperm DNA. Hybridization could occur under reduced stringency conditions as described above, but in 35% formamide or/and at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of HUCS, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative", changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of a new human citrate synthase homolog (hereinafter referred to as "HUCS"), the polynucleotides encoding HUCS, and the use of these compositions for the diagnosis, prevention, or treatment of cancer, inflammatory disorders, and disorders of the sympathetic nervous system.

Nucleic acids encoding the HUCS of the present invention were first identified in Incyte Clone 2171653 from the dermal microvascular endothelial cell cDNA library END-CNOT03 using a computer search for amino acid sequence alignments. A consensus sequence, SEQ ID NO:2, was derived from the following overlapping and/or extended nucleic acid sequences: Incyte Clones 063049 and 063874 (PLACNOB01), 262873 (HNT2AGT01), 1208638 (BRSTNOT02), 1229157 (BRAITUT01), 1424489 (BEPINON01), 2016438 and 2171653 (ENDCNOT03), 2370732 (ADRENOT07), and 2620394 (KERANOT02).

In one embodiment, the invention encompasses a polypeptide comprising the amino acid sequence of SEQ ID NO:1, as shown in FIGS. 1A–F. HUCS is 466 amino acids in length and has potential casein kinase II phosphorylation sites at S83, S97, T153, S232, and S263. HUCS has potential protein kinase C phosphorylation sites at T50 and S338 and potential tyrosine kinase phosphoryation sites at K193 and R351. HUCS has a potential citrate synthase signature sequence at G344. As shown in FIGS. 2A–B, HUCS has chemical and structural homology with pig citrate synthase precursor (GI 164419; SEQ ID NO:3). In particular, HUCS and pig citrate synthase precursor share 96% identity. HUCS and pig citrate synthase precursor share 100% identity in the citrate synthase signature sequence at G344. HUCS and pig citrate synthase precursor share 93% identity in the first 27 amino acids, the mitochondrial leader sequence of pig citrate synthase precursor. Northern analysis shows the expression of this sequence in various libraries, at least 40% of which are cancerous, 31% are inflammatory, and 2% are neurological. Of particular note is the expression of HUCS in cancerous, inflammatory, and neurological tissues.

The invention also encompasses HUCS variants. A preferred HUCS variant is one having at least 80%, and more preferably at least 90%, amino acid sequence identity to the HUCS amino acid sequence (SEQ ID NO:1) and which retains at least one biological, immunological or other fluctional characteristic or activity of HUCS. A most preferred HUCS variant is one having at least 95% amino acid sequence identity to SEQ ID NO:1.

The invention also encompasses a polynucleotide sequence which encodes HUCS. Accordingly, any nucleic acid sequence which encodes the amino acid sequence of HUCS can be used to produce recombinant molecules which express HUCS. In a particular embodiment, the invention encompasses the polynucleotide comprising the nucleic acid sequence of SEQ ID NO:2 as shown in FIGS. 1A–F.

The invention also encompasses a variant of a polynucleotide sequence encoding HUCS. In particular, such a variant polynucleotide sequence will have at least about 80%, more preferably at least about 90%, and most preferably at least about 95% polynucleotide sequence identity to the polynucleotide sequence encoding HUCS. A particular aspect of the invention encompasses a variant of SEQ ID NO:2 which has about 80%, more preferably at least about 90%, and most preferably at least about 95% polynucleotide sequence identity to SEQ ID NO:2.

It will be appreciated by those skilled in the art that as a result of the degeneracy of the genetic code, a multitude of nucleotide sequences encoding HUCS, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HUCS, and all such variations are to be considered as being specifically disclosed.

Although nucleotide sequences which encode HUCS and its variants are preferably capable of hybridizing to the nucleotide sequence of the naturally occurring HUCS under appropriately selected conditions of stringency, it may be advantageous to produce nucleotide sequences encoding HUCS or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HUCS and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode HUCS and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HUCS or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399–407) and Kimmel, A. R. (1987; Methods Enzymol. 152:507511).

Methods for DNA sequencing which are well known and generally available in the art and may be used to practice any of the embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding HUCS may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HUCS may be used in recombinant DNA molecules to direct expression of HUCS, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HUCS.

As will be understood by those of skill in the art, it may be advantageous to produce HUCS-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HUCS encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HUCS may be ligated to a heterologous sequence to encode a fusion protein. For example, to screen peptide libraries for inhibitors of HUCS activity, it may be useful to encode a chimeric HUCS protein that can be recognized by a commercially available antibody. A fusion protein may also be engineered to contain a cleavage site located between the HUCS encoding sequence and the heterologous protein sequence, so that HUCS may be cleaved and purified away from the heterologous moiety.

In another embodiment, sequences encoding HUCS may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of HUCS, or a fragment thereof. For example, peptide synthesis can be performed using various solid-phase techniques (Roberge, J. Y. et.al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of HUCS, or any part thereof, may be altered during direct synthesis and/or combined using chemical methods with sequences from other proteins, or any part thereof, to produce a variant polypeptide.

In order to express a biologically active HUCS, the nucleotide sequences encoding HUCS or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding HUCS and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding HUCS. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or psport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HUCS, vectors based on SV40 or EBV may be used with an appropriate selectable marker.

In bacterial systems, a number of expression vectors may be selected depending upon the use intended for HUCS. For example, when large quantities of HUCS are needed for the induction of antibodies, vectors which direct high level expression of fusion proteins that are readily purified may be used. Such vectors include, but are not limited to, the multifinctional *E. coli* cloning and expression vectors such. as Bluescript® (Stratagene), in which the sequence encoding HUCS may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding HUCS may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express HUCS. For example, in one such system, *Autographa californica* nuclear polyhedrosis virus (AcNPV) is used as a vector to express foreign genes in *Spodoptera frugiperda* cells or in Trichoplusia larvae. The sequences encoding HUCS may be cloned into a non-essential region of the virus, such as the polyhedrin gene, and placed under control of the polyhedrin promoter. Successful insertion of HUCS will render the polyhedrin gene inactive and produce recombinant virus lacking coat protein. The recombinant viruses may then be used to infect, for example, *S. frugiperda* cells or Trichoplusia larvae in which HUCS may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding HUCS may be ligated into an adenovirus transcription/translation complex consisting of the late promoter and tripartite leader sequence. Insertion in a non-essential E1 or E3 region of the viral genome may be used to obtain a viable virus which is capable of expressing HUCS in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding HUCS. Such signals include the ATG initiation codon and adjacent sequences. In cases where sequences encoding HUCS, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express HUCS may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$ or $aprt^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding HUCS is inserted within a marker gene sequence, transformed cells containing sequences encoding HUCS can be identified by the absence of marker gene function. Alternatively, a marker gene can be placed in tandem with a sequence encoding HUCS under the control of a single promoter. Expression of the marker gene in response to induction or selection usually indicates expression of the tandem gene as well.

Alternatively, host cells which contain the nucleic acid sequence encoding HUCS and express HUCS may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding HUCS can be detected by DNA-DNA or DNA-RNA hybridization or amplification using probes or fragments or fragments of polynucleotides encoding HUCS. Nucleic acid amplification based assays involve the use of oligonucleotides or oligomers based on the sequences encoding HUCS to detect transformants containing DNA or RNA encoding HUCS.

A variety of protocols for detecting and measuring the expression of HUCS, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HUCS is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HUCS include oligolabeling, nick translation, end-labeling or PCR amplification using a labeled nucleotide. Alternatively, the sequences encoding HUCS, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding HUCS may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HUCS may be designed to contain signal sequences which direct secretion of HUCS through a prokaryotic or eukaryotic cell membrane. Other constructions may be used to join sequences encoding HUCS to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HUCS may be used to facilitate purification. One such expression vector provides for expression of a fusion protein containing HUCS and a nucleic acid encoding 6 histidine residues preceding a thioredoxin or an enterokinase cleavage site. The histidine residues facilitate purification on IMAC (immobilized metal ion affinity chromatography as described in Porath, J. et al. (1992, Prot. Exp. Purif. 3: 263–281) while the enterokinase cleavage site provides a means for purifying HUCS from the fusion protein. A discussion of vectors which contain fusion proteins is provided in Kroll, D. J. et al. (1993; DNA Cell Biol. 12:441–453).

In addition to recombinant production, fragments of HUCS may be produced by direct peptide synthesis using solid-phase techniques Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of HUCS may be chemically synthesized separately and combined using chemical methods to produce the full length molecule.

THERAPEUTICS

Chemical and structural homology exists between HUCS and pig citrate synthase precursor (GI 164419). In addition, HUCS is expressed in cancerous, inflamed, and neurological tissues. Therefore, HUCS appears to play a role in cancer, inflammatory disorders, and disorders of the sympathetic nervous system.

In one embodiment, HUCS or a fragment or derivative thereof may be administered to a subject to prevent or treat a cancer. Cancers may include, but are not limited to, adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector capable of expressing HUCS, or a fragment or a derivative thereof, may also be administered to a subject to prevent or treat a cancer including, but not limited to, those described above.

In still another embodiment, an agonist which modulates the activity of HUCS may also be administered to a subject to prevent or treat a cancer including, but not limited to, those described above.

In one embodiment, HUCS or a fragment or derivative thereof may be administered to a subject to prevent or treat an inflammatory disorder. Such disorders include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, pyelonephritis, rheumatoid arthritis, scleroderma, Sjögren's syndrome, and autoimmune thyroiditis; complications of cancer, hemodialysis, and extracorporeal circulation; viral, bacterial, fungal, parasitic, protozoal, and helminthic infections; and trauma.

In another embodiment, a vector capable of expressing HUCS, or a fragment or a derivative thereof, may also be administered to a subject to prevent or treat an inflammatory disorder including, but not limited to, those described above.

In still another embodiment, an agonist which modulates the activity of HUCS may also be administered to a subject to prevent or treat an inflammatory disorder including, but not limited to, those described above.

In one embodiment, HUCS or a fragment or derivative thereof may be administered to a subject to prevent or treat a disorder of the sympathetic nervous system. Such disorders include, but are not limited to, angina, anaphylactic shock, arrhythmias, asthma, cardiovascular shock, Cushing's syndrome, hypertension, hypoglycemia, myocardial infarction, migraine, and pheochromocytoma.

In another embodiment, a vector capable of expressing HUCS, or a fragment or a derivative thereof, may also be administered to a subject to prevent or treat a disorder of the sympathetic nervous system including, but not limited to, those described above.

In still another embodiment, an agonist which modulates the activity of HUCS may also be administered to a subject to prevent or treat a disorder of the sympathetic nervous system including, but not limited to, those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HUCS may be produced using methods which are generally known in the art. In particular, purified HUCS may be used to produce antibodies or to screen libraries of pharmaceutical agents to identify those which specifically bind HUCS.

Antibodies to HUCS may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HUCS or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HUCS have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of HUCS amino acids may be fused with those of another protein such as keyhole limpet hemocyanin and antibody produced against the chimeric molecule.

Monoclonal antibodies to HUCS may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce HUCS-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for HUCS may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HUCS and its specific antibody. A two-site, monoclonal-based immunoassay utilizing monoclonal antibodies reactive to two non-interfering HUCS epitopes is preferred, but a competitive binding assay may also be employed (Maddox, supra).

In another embodiment of the invention, the polynucleotides encoding HUCS, or any fragment or complement thereof, may be used for therapeutic purposes. In one aspect, the complement of the polynucleotide encoding HUCS may be used in situations in which it would be desirable to block the transcription of the mRNA. In particular, cells may be transformed with sequences complementary to polynucleotides encoding HUCS. Thus, complementary molecules or fragments may be used to modulate HUCS activity, or to achieve regulation of gene function. Such technology is now well known in the art, and sense or antisense oligonucleotides or larger fragments, can be designed from various locations along the coding or control regions of sequences encoding HUCS.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding HUCS. These techniques are described both in Sambrook et al. (supra) and in Ausubel et al. (supra).

Genes encoding HUCS can be turned off by transforming a cell or tissue with expression vectors which express high levels of a polynucleotide or fragment thereof which encodes HUCS. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding HUCS (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HUCS.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HUCS. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HUCS, antibodies to HUCS, mimetics, agonists, antagonists, or inhibitors of HUCS. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HUCS, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HUCS or fragments thereof, antibodies of HUCS, agonists, antagonists or inhibitors of HUCS, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HUCS may be used for the diagnosis of conditions or diseases characterized by expression of HUCS, or in assays to monitor patients being treated with HUCS, agonists, antagonists or inhibitors. The antibodies useful for diagnostic purposes may be prepared in the same manner as those described above for therapeutics. Diagnostic assays for HUCS include methods which utilize the antibody and a label to detect HUCS in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HUCS are known in the art and provide a basis for diagnosing altered or abnormal levels of HUCS expression. Normal or standard values for HUCS expression are established by combining body fluids or cell extracts taken from normal mammalian subjects, preferably human, with antibody to HUCS under conditions suitable for complex formation The amount of standard complex formation may be quantified by various methods, but preferably by photometric, means. Quantities of HUCS expressed in subject, control and disease, samples from biopsied tissues are compared with the standard values. Deviation between standard and subject values establishes the parameters for diagnosing disease.

In another embodiment of the invention, the polynucleotides encoding HUCS may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HUCS may be correlated with disease. The diagnostic assay may be used to distinguish between absence, presence, and excess expression of HUCS, and to monitor regulation of HUCS levels during therapeutic intervention.

In one aspect, hybridization with PCR probes which are capable of detecting polynucleotide sequences, including genomic sequences, encoding HUCS or closely related molecules, may be used to identify nucleic acid sequences which encode HUCS. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HUCS, alleles, or related sequences.

Probes may also be used for the detection of related sequences, and should preferably contain at least 50% of the nucleotides from any of the HUCS encoding sequences. The hybridization probes of the subject invention may be DNA or RNA and derived from the nucleotide sequence of SEQ ID NO:2 or from genomic sequence including promoter, enhancer elements, and introns of the naturally occurring HUCS.

Means for producing specific hybridization probes for DNAs encoding HUCS include the cloning of nucleic acid sequences encoding HUCS or HUCS derivatives into vectors for the production of MRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as $^{32}$P or 35S, or enzymatic labels, such as alkaline phosphatase coupled to the probe via avidin/biotin coupling systems, and the like.

Polynucleotide sequences encoding HUCS may be used for the diagnosis of conditions or disorders which are associated with expression of HUCS. Examples of such conditions or disorders include: cancer, including adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; inflammatory disorders including AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, pyelonephritis, rheumatoid arthritis, scleroderma, Sjögren's syndrome, and autoimmune thyroiditis; complications of cancer, hemodialysis, and extracorporeal circulation; viral, bacterial, fungal, parasitic, protozoal, and helminthic infections; and trauma; and disorders of the sympathetic nervous system, including angina, anaphylactic shock, arrhythmias, asthma, cardiovascular shock, Cushing's syndrome, hypertension, hypoglycemia, myocardial infarction, migraine, and pheochromocytoma. The polynucleotide sequences encoding HUCS may be used in Southern or northern analysis, dot blot, or other membrane-based technologies; in PCR technologies; or in dipstick, pin, ELISA assays or microarrays utilizing fluids or tissues from patient biopsies to detect altered HUCS expression. Such qualitative or quantitative methods are well known in the art.

In a particular aspect, the nucleotide sequences encoding HUCS may be useful in assays that detect activation or induction of various cancers, particularly those mentioned above. The nucleotide sequences encoding HUCS may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding HUCS in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HUCS, a normal or standard profile for expression is established. This may be accomplished by combining body fluids or cell extracts taken from normal subjects, either animal or human, with a sequence, or a fragment thereof, which encodes HUCS, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HUCS may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HUCS include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or calorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode HUCS may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding HUCS on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HUCS, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HUCS and the agent being tested, may be measured.

Another technique for drug screening which may be used provides for high throughput screening of compounds having suitable binding affinity to the protein of interest as described in published PCT application WO84/03564. In this method, as applied to HUCS large numbers of different small test compounds are synthesized on a solid substrate, such as plastic pins or some other surface. The test compounds are reacted with HUCS, or fragments thereof, and washed. Bound HUCS is then detected by methods well known in the art. Purified HUCS can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HUCS specifically compete with a test compound for binding HUCS. In this manner, the antibodies can be used to detect the presence of any peptide which shares one or more antigenic determinants with HUCS.

In additional embodiments, the nucleotide sequences which encode HUCS may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I ENDCNOT03 cDNA Library Construction

The ENDCNOT03 cDNA library was constructed from a dermal endothelial cell line obtained from a Caucasian male (specimen #CC-2605; Clonetics Corp., San Diego, Calif.). Endothelial cells (50–100 mg) were homogenized for 1–2 minutes in 0.4 ml GTC homogenization buffer (4.0M guanidine thiocyanate, 0.1M Tris-HCl pH 7.5, 1% 2-mercaptoethanol). Two volumes of binding buffer (0.4M LiCl, 0.1M Tris-HCl pH 7.5, 0.02M EDTA) were added and the resulting mixture vortexed. Following centrifugation at 13,000 rpm for 45 seconds to 1.5 minutes, the supernatant was removed and combined with Oligo(dT)$_{25}$ (product #MBOLG; CPG) bound MPG streptavidin particles (product #MSTR0502; CPG). After 25–30 minutes of 360° rotation at room temperature, the mRNA-Oligo(dT)$_{25}$-streptavidin particles were separated from the supernatant, washed twice with hybridization buffer I (0.15M NaCl, 0.01M Tris-HCl pH 8.0, 1 mM EDTA, 0.1% lauryl sarcosinate) and washed twice with hybridization buffer II (0.15M NaCl, 0.01M Tris-HCl pH 8.0, 1 mM EDTA) using magnetic separation at each step to remove the supernatant from the particles. Bound mRNA was eluted from the MPG streptavidin particles with release solution (5 mM Tris-HCl, pH 7.5) and heating to 65° for 2 minutes. The supernatant containing eluted mRNA was magnetically separated from the streptavidin particles and used to construct the cDNA library.

The mRNA was handled according to the recommended protocols in the SuperScript Plasmid System for cDNA synthesis and plasmid cloning (Cat. #18248-013; Gibco/BRL). The cDNAs were fractionated on a Sepharose CL4B column (Cat. #275105-01; Pharmacia), and those cDNAs exceeding 400 bp were ligated into pINCY 1. The plasmid pINCY 1 was subsequently transformed into DH5α™ competent cells (Cat. #18258-012; Gibco/BRL).

II Isolation and Sequencing of cDNA Clones

Plasmid DNA was released from the cells and purified using the REAL Prep 96 plasmid kit (Catalog #26173; QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems. The reading frame was determined.

III Homology Searching of cDNA Clones and Their Deduced Proteins

The nucleotide sequences and/or amino acid sequences were used as query sequences against databases such as GenBank, SwissProt, BLOCKS, and Pima II. These databases, which contain previously identified and annotated sequences, were searched for regions of homology using BLAST, which stands for Basic Local Alignment Search Tool (Altschul, S. F. (1993) J. Mol. Evol.. 36:290–300; Altschul, S. F., et al. (1990) J. Mol. Biol. 215:403–410).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smit, T. et al. (1992, Protein Engineering 5:35–51), incorporated herein by reference, could have been used when dealing with primary sequence patterns and secondary structure gap penalties. The sequences disclosed in this application have lengths of at least 49 nucleotides, and no more than 12% uncalled bases (where N is recorded rather than A,C, G,or T).

The BLAST approach searched for matches between a query sequence and a database sequence. BLAST evaluated the statistical significance of any matches found and reported only those matches that satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and other mammalian sequences (mam); and deduced amino acid sequences from the same clones were then searched against GenBank functional protein databases, mammalian (mamp), vertebrate (vrtp), and eukaryote (eukp) for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) supra; Altschul, S. F. et al. (1990) supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HUCS occurs. Abundance and percent abundance are also reported. Abundance directly reflects the number of times a particular transcript is represented in a cDNA library, and percent abundance is abundance divided by the total number of sequences examined in the cDNA library.

V Extension of HUCS Encoding Polynucleotides

The nucleic acid sequence of the Incyte Clone 2171653 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M. J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQuick™ (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent E. coli cells (in 40 μl of appropriate media) were transformed with 3 μl of ligation mixture and cultured in 80 μl of SOC medium (Sambrook et al., supra). After incubation for one hour at 37° C., the E. coli mixture was plated on Luria Bertani (LB)-agar (Sambrook et al., supra) containing 2× Carb. The following day, several colonies were randomly picked from each plate and cultured in 150 μl of liquid LB/2× Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 μCi of [γ-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots in a PhosphorImager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the HUCS-encoding sequence, or any part thereof, is used to decrease or inhibit expression of naturally occurring HUCS. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of HUCS, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HUCS-encoding transcript.

IX Expression of HUCS

Expression of HUCS is accomplished by subcloning the cDNAs into appropriate vectors and transforming the vectors into host cells. In this case, the cloning vector is also used to express HUCS in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HUCS into the bacterial growth media which can be used directly in the following assay for activity.

X Demonstration of HUCS Activity

HUCS activity in a sample is assayed by measuring production of CoASH (Srere, P. A. (1969) Meth. Enzymol. 13:3–11). The assay is carried out in an optical cuvette containing sample, 5, 5'-dithiobis-(2-nitrobenzoate) (DTNB or Ellman's reagent), acetyl-CoA, oxaloacetate, and water. CoASH reacts with DTNB to form a yellow-colored aromatic thiol. The amount of thiol formed is measured by absorption at 412 run using a spectrophotometer and is proportional to the activity of HUCS in the sample.

XI Production of HUCS Specific Antibodies

HUCS that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 43 1A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring HUCS Using Specific Antibodies

Naturally occurring or recombinant HUCS is substantially purified by immunoaffinity chromatography using antibodies specific for HUCS. An immunoaffinity column is constructed by covalently coupling HUCS antibody to an activated chromatographic resin, such as CNBr-activated Sepharose (Pharmacia & Upjohn). After the coupling, the resin is blocked and washed according to the manufacturer's instructions.

Media containing HUCS is passed over the immunoaffinity column, and the column is washed under conditions that allow the preferential absorbance of HUCS (e.g., high ionic strength buffers in the presence of detergent). The column is eluted under conditions that disrupt antibody/HUCS binding (e.g., a buffer of pH 2–3 or a high concentration of a chaotrope, such as urea or thiocyanate ion), and HUCS is collected.

XIII Identification of Molecules Which Interact with HUCS

HUCS or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled HUCS, washed and any wells with labeled HUCS complex are assayed. Data obtained using different concentrations of HUCS are used to calculate values for the number, affinity, and association of HUCS with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding the human citrate synthase homolog (HUCS) of SEQ ID NO:1.

2. A composition comprising the polynucleotide sequence of claim 1.

3. An isolated and purified polynucleotide sequence which is completely complementary to the polynucleotide sequence of claim 1.

4. An isolated and purified polynucleotide sequence consisting of SEQ ID NO:2.

5. An isolated and purified polynucleotide sequence which is completely complementary to the polynucleotide sequence of claim 4.

6. An expression vector containing the polynucleotide sequence of claim 1.

7. A host cell containing the expression vector of claim 6.

8. A method for producing a polypeptide consisting of the amino acid sequence of SEQ ID NO:1, the method comprising the steps of:

a) culturing the host cell of claim 7 under conditions suitable for the expression of the polypeptide; and b) recovering the polypeptide from the host cell culture.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 466 amino acids
      (B) TYPE: amino acid
      (C) STRANDEDNESS: single
      (D) TOPOLOGY: linear (vii) IMMEDIATE SOURCE:
      (A) LIBRARY: ENDCNOT03
      (B) CLONE: 2171653

(xi) SEQUENCE DESCRIPTION: SEQ ID NO:1:

```
Met Ala Leu Leu Thr Ala Ala Ala Arg Leu Leu Gly Thr Lys Asn Ala
 1               5                  10                  15

Ser Cys Leu Val Leu Ala Ala Arg His Ala Ser Ala Ser Ser Thr Asn
                20                  25                  30

Leu Lys Asp Ile Leu Ala Asp Leu Ile Pro Lys Glu Gln Ala Arg Ile
            35                  40                  45

Lys Thr Phe Arg Gln Gln His Gly Lys Thr Val Val Gly Gln Ile Thr
        50                  55                  60

Val Asp Met Met Tyr Gly Gly Met Arg Gly Met Lys Gly Leu Val Tyr
65                  70                  75                  80
```

-continued

```
Glu Thr Ser Val Leu Asp Pro Asp Glu Gly Ile Arg Phe Arg Gly Phe
                85                  90                  95

Ser Ile Pro Glu Cys Gln Lys Leu Leu Pro Lys Ala Lys Gly Gly Glu
            100                 105                 110

Glu Pro Leu Pro Glu Gly Leu Phe Trp Leu Val Thr Gly His Ile
        115                 120                 125

Pro Thr Glu Glu Gln Val Ser Trp Leu Ser Lys Glu Trp Ala Lys Arg
    130                 135                 140

Ala Ala Leu Pro Ser His Val Val Thr Met Leu Asp Asn Phe Pro Thr
145                 150                 155                 160

Asn Leu His Pro Met Ser Gln Leu Ser Ala Ala Val Thr Ala Leu Asn
                165                 170                 175

Ser Glu Ser Asn Phe Ala Arg Ala Tyr Ala Gln Gly Ile Ser Arg Thr
            180                 185                 190

Lys Tyr Trp Glu Leu Ile Tyr Glu Asp Ser Met Asp Leu Ile Ala Lys
        195                 200                 205

Leu Pro Cys Val Ala Ala Lys Ile Tyr Arg Asn Leu Tyr Arg Glu Gly
    210                 215                 220

Ser Gly Ile Gly Ala Ile Asp Ser Asn Leu Asp Trp Ser His Asn Phe
225                 230                 235                 240

Thr Asn Met Leu Gly Tyr Thr Asp His Gln Phe Thr Glu Leu Thr Arg
                245                 250                 255

Leu Tyr Leu Thr Ile His Ser Asp His Glu Gly Gly Asn Val Ser Ala
            260                 265                 270

His Thr Ser His Leu Val Gly Ser Ala Leu Ser Asp Pro Tyr Leu Ser
        275                 280                 285

Phe Ala Ala Ala Met Asn Gly Leu Ala Gly Pro Leu His Gly Leu Ala
    290                 295                 300

Asn Gln Glu Val Leu Val Trp Leu Thr Gln Leu Gln Lys Glu Val Gly
305                 310                 315                 320

Lys Asp Val Ser Asp Glu Lys Leu Arg Asp Tyr Ile Trp Asn Thr Leu
                325                 330                 335

Asn Ser Gly Arg Val Val Pro Gly Tyr Gly His Ala Val Leu Arg Lys
            340                 345                 350

Thr Asp Pro Arg Tyr Thr Cys Gln Arg Glu Phe Ala Leu Lys His Leu
        355                 360                 365

Pro Asn Asp Pro Met Phe Lys Leu Val Ala Gln Leu Tyr Lys Ile Val
    370                 375                 380

Pro Asn Val Leu Leu Glu Gln Gly Lys Ala Lys Asn Pro Trp Pro Asn
385                 390                 395                 400

Val Asp Ala His Ser Gly Val Leu Leu Gln Tyr Tyr Gly Met Thr Glu
                405                 410                 415

Met Asn Tyr Tyr Thr Val Leu Phe Gly Val Ser Arg Ala Leu Gly Val
            420                 425                 430

Leu Ala Gln Leu Ile Trp Ser Arg Ala Leu Gly Phe Pro Leu Glu Arg
        435                 440                 445

Pro Lys Ser Met Ser Thr Glu Gly Leu Met Lys Phe Val Asp Ser Lys
    450                 455                 460

Ser Gly
465
```

(2) INFORMATION FOR SEQ ID NO:2:

(i) SEQUENCE CHARACTERISTICS:
        (A) LENGTH: 2131 base pairs
        (B) TYPE: nucleic acid
        (C) STRANDEDNESS: single
        (D) TOPOLOGY: linear (vii) IMMEDIATE SOURCE:
        (A) LIBRARY: ENDCNOT03
        (B) CLONE: 2171653

(xi) SEQUENCE DESCRIPTION: SEQ ID NO:2:

```
CGCCGGTTCG TCTACTCTTT CCTTCAGCCG CCTCCTTTCA ACCTTGTCAA CCCGTCGGCG      60
CGGCCTCTGG TGCAGCGGCG GCGGCTCCTG TTCCTGCCGC AGCTCTCTCC CTTTCTTACC     120
TCCCCACCAG ATCCCGGAGA TCGCCCGCCA TGGCTTTACT TACTGCGGCC GCCCGGCTCT     180
TGGGAACCAA GAATGCATCT TGTCTTGTTC TTGCAGCCCG GCATGCCAGT GCTTCCTCCA     240
CGAATTTGAA AGACATATTG GCTGACCTGA TACCTAAGGA GCAGGCCAGA ATTAAGACTT     300
TCAGGCAGCA ACATGGCAAG ACGGTGGTGG GCCAAATCAC TGTGGACATG ATGTATGGTG     360
GCATGAGAGG CATGAAGGGA TTGGTCTATG AAACATCAGT TCTTGATCCT GATGAGGGCA     420
TCCGTTTCCG AGGCTTTAGT ATCCCTGAAT GCCAGAAACT GCTACCCAAG GCTAAGGGTG     480
GGAAGAACC CCTGCCTGAG GGCTTATTTT GGCTGCTGGT AACTGGACAT ATCCCAACAG      540
AGGAACAGGT ATCTTGGCTC TCAAAAGAGT GGGCAAAGAG GGCAGCTCTG CCTTCCCATG     600
TGGTCACCAT GCTGGACAAC TTTCCCACCA ATCTACACCC CATGTCTCAG CTCAGTGCAG     660
CTGTTACAGC CCTAACAGT GAAAGTAACT TTGCCCGAGC ATATGCACAG GGTATCAGCC      720
GAACCAAGTA CTGGGAGTTG ATTTATGAAG ACTCTATGGA TCTAATCGCA AAGCTACCTT     780
GTGTTGCAGC AAAGATCTAC CGAAATCTCT ACAGAGAAGG CAGCGGTATT GGGGCCATTG     840
ACTCTAACCT GGACTGGTCT CACAATTTCA CCAACATGTT AGGCTATACT GATCATCAGT     900
TCACTGAGCT CACGCGCCTG TACCTCACCA TCCACAGTGA CCATGAGGGT GGCAATGTAA     960
GTGCCCATAC CAGCCATTTG GTGGGCAGTG CCCTTTCCGA CCCTTACCTG TCCTTTGCAG    1020
CAGCCATGAA CGGGCTGGCA GGGCCTCTCC ATGGACTGGC AAATCAGGAA GTGCTTGTCT    1080
GGCTAACACA GCTGCAGAAG GAAGTTGGCA AGATGTGTC AGATGAGAAG TTACGAGACT     1140
ACATCTGGAA CACACTCAAC TCAGGACGGG TTGTTCCAGG CTATGGCCAT GCAGTACTAA    1200
GGAAGACTGA TCCGCGATAT ACCTGTCAGC GAGAGTTTGC TCTGAAACAC CTGCCTAATG    1260
ACCCCATGTT TAAGTTGGTT GCTCAGCTGT ACAAGATTGT GCCCAATGTC CTCTTAGAGC    1320
AGGGTAAAGC CAAGAATCCT TGGCCCAATG TAGATGCTCA CAGTGGGGTG CTGCTCCAGT    1380
ATTATGGCAT GACGGAGATG AATTACTACA CGGTCCTGTT TGGGGTGTCA CGAGCATTGG    1440
GTGTACTGGC ACAGCTCATC TGGAGCCGAG CCTTAGGCTT CCCTCTAGAA AGGCCCAAGT    1500
CCATGAGCAC AGAGGGTCTG ATGAAGTTTG TGGACTCTAA GTCAGGGTAA AACTGGAGAC    1560
TGGGTGAAAG TGACTACCAG AAAGTGAGGA AGCCTAAATA AAAAGTATAC TTTTGTTTCA    1620
GGGGGCCTTT AAAGACTTAA GATTAAATTA TATCTGAGGC ACTGATAATA TGTTTGAGGT    1680
TAAAATATAA ATTAAGACTT TAAAAGATGA AAAATGGTCC CTTCTTCCCT AATCAGCTCC    1740
CTTCCCCTGC CTGGTATGAG TTGCCCATCA TACGCATGGT CCTGGAGGAT GACCAGGACT    1800
AATGCATGTG GTATGAGTAG GTTTGGCCCC CTCACTATCT CTAGAGTGAG AATCTGGCTC    1860
CTGTTTCCAT GGGTCAAAGC CGGTTGCAGA GAATCTGTAG TCACTTTGGA GCTTTAGCTT    1920
```

```
CTCTGCCAAG CCCTCAATAA GCCAGCAAAC CAGGACTCTG CCCCTTCTGT TTCCATAGGA      1980

ATCATGTTGG ATAGTCAGCT GTACCAAGCC CCTTGGCCCT CTCCCATGCA CACAAACACC      2040

TCCTAGCAAG ACCTGTTGGT TAGCTGGACA TGCTTTGGCA ATTTTTTTAT ACTACCAAGT      2100

GACCATATTG GCATGGCATT TTTTGGTGAT G                                     2131
```

(2) INFORMATION FOR SEQ ID NO:3:

(i) SEQUENCE CHARACTERISTICS:
        (A) LENGTH: 464 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 164419

(xi) SEQUENCE DESCRIPTION: SEQ ID NO:3:

```
Met Ala Leu Leu Thr Ala Ala Arg Leu Phe Gly Ala Lys Asn Ala
 1               5                  10                  15

Ser Cys Leu Val Leu Ala Ala Arg His Ala Ser Ala Ser Thr Asn
                20                  25                  30

Leu Lys Asp Ile Leu Ala Asp Leu Ile Pro Lys Glu Gln Ala Arg Ile
        35                  40                  45

Lys Thr Phe Arg Gln Gln His Gly Asn Thr Val Val Gly Gln Ile Thr
    50                  55                  60

Val Asp Met Met Tyr Gly Gly Met Arg Gly Met Lys Gly Leu Val Tyr
65                  70                  75                  80

Glu Thr Ser Val Leu Asp Pro Asp Glu Gly Ile Arg Phe Arg Gly Tyr
                85                  90                  95

Ser Ile Pro Glu Cys Gln Lys Met Leu Pro Lys Ala Lys Gly Gly Glu
            100                 105                 110

Glu Pro Leu Pro Glu Gly Leu Phe Trp Leu Leu Val Thr Gly Gln Ile
        115                 120                 125

Pro Thr Glu Glu Gln Val Ser Trp Leu Ser Lys Glu Trp Ala Lys Arg
    130                 135                 140

Ala Ala Leu Pro Ser His Val Val Thr Met Leu Asp Asn Phe Pro Thr
145                 150                 155                 160

Asn Leu His Pro Met Ser Gln Leu Ser Ala Ala Ile Thr Ala Leu Asn
                165                 170                 175

Ser Glu Ser Asn Phe Ala Arg Ala Tyr Ala Glu Gly Ile His Arg Thr
            180                 185                 190

Lys Tyr Trp Glu Leu Ile Tyr Glu Asp Cys Met Asp Leu Ile Ala Lys
        195                 200                 205

Leu Pro Cys Val Ala Ala Lys Ile Tyr Arg Asn Leu Tyr Arg Glu Gly
    210                 215                 220

Ser Ser Ile Gly Ala Ile Asp Ser Lys Leu Asp Trp Ser His Asn Phe
225                 230                 235                 240

Thr Asn Met Leu Gly Tyr Thr Asp Ala Gln Phe Thr Glu Leu Met Arg
                245                 250                 255

Leu Tyr Leu Thr Ile His Ser Asp His Glu Gly Gly Asn Val Ser Ala
            260                 265                 270

His Thr Ser His Leu Val Gly Ser Ala Leu Ser Asp Pro Tyr Leu Ser
        275                 280                 285
```

-continued

```
Phe Ala Ala Ala Met Asn Gly Leu Ala Gly Pro Leu His Gly Leu Ala
    290                 295                 300

Asn Gln Glu Val Leu Val Trp Leu Thr Gln Leu Gln Lys Glu Val Gly
305                 310                 315                 320

Lys Asp Val Ser Asp Glu Lys Leu Arg Asp Tyr Ile Trp Asn Thr Leu
                325                 330                 335

Asn Ser Gly Arg Val Val Pro Gly Tyr Gly His Ala Val Leu Arg Lys
                340                 345                 350

Thr Asp Pro Arg Tyr Thr Cys Gln Arg Glu Phe Ala Leu Lys His Leu
            355                 360                 365

Pro His Asp Pro Met Phe Lys Leu Val Ala Gln Leu Tyr Lys Ile Val
        370                 375                 380

Pro Asn Val Leu Leu Glu Gln Gly Lys Ala Lys Asn Pro Trp Pro Asn
385                 390                 395                 400

Val Asp Ala His Ser Gly Val Leu Leu Gln Tyr Tyr Gly Met Thr Glu
                405                 410                 415

Met Asn Tyr Tyr Thr Val Leu Phe Gly Val Ser Arg Ala Leu Gly Val
            420                 425                 430

Leu Ala Gln Leu Ile Trp Ser Arg Ala Leu Gly Phe Pro Leu Glu Arg
        435                 440                 445

Pro Lys Ser Met Ser Thr Asp Gly Leu Ile Lys Leu Val Asp Ser Lys
    450                 455                 460
```